US012766297B2

(12) United States Patent
Edgar et al.

(10) Patent No.: US 12,766,297 B2
(45) Date of Patent: Oct. 20, 2026

(54) DEVICE AND METHOD FOR CONTINUOUS EVEN APPLICATION OF COMPOSITION TO SKIN

(71) Applicant: Kenvue Brands LLC, Summit, NJ (US)

(72) Inventors: Albert Durr Edgar, Austin, TX (US); Laura Higgins, Boston, MA (US)

(73) Assignee: Kenvue Brands LLC, Summit, NJ (US)

( * ) Notice: Subject to any disclaimer, the term of this patent is extended or adjusted under 35 U.S.C. 154(b) by 1002 days.

(21) Appl. No.: 17/538,483

(22) Filed: Nov. 30, 2021

(65) Prior Publication Data

US 2022/0193381 A1 Jun. 23, 2022

Related U.S. Application Data

(60) Provisional application No. 63/199,354, filed on Dec. 21, 2020.

(51) Int. Cl.
*A61M 35/00* (2006.01)
*G06T 7/00* (2017.01)

(52) U.S. Cl.
CPC ......... *A61M 35/003* (2013.01); *G06T 7/0014* (2013.01); *A61M 2205/52* (2013.01); *G06T 2207/30088* (2013.01)

(58) Field of Classification Search
CPC .............. A45D 2044/007; A45D 34/04; A45D 44/005; A61B 5/0064; A61B 5/0082;
(Continued)

(56) References Cited

U.S. PATENT DOCUMENTS

| | | | |
|---|---|---|---|
| 6,149,719 | A | 11/2000 | Houle |
| 7,642,062 | B2 | 1/2010 | Dryer et al. |

(Continued)

FOREIGN PATENT DOCUMENTS

| | | |
|---|---|---|
| CN | 101287607 | 10/2008 |
| CN | 101573101 | 11/2009 |

(Continued)

OTHER PUBLICATIONS

International Search Report and Written Opinion mailed on Nov. 16, 2021 in corresponding International Application No. PCT/US2021/071079.

(Continued)

*Primary Examiner* — James D Ponton
*Assistant Examiner* — Hong-Van N Trinh
(74) *Attorney, Agent, or Firm* — Wan Chieh Lee; Haug Partners LLP

(57) ABSTRACT

A device and method for selectively applying a composition to a treatment surface (e.g., skin) to alter an aesthetic appearance of the skin. The device includes a detector obtaining image data corresponding to an image of an area of skin and an applicator applying the composition to the skin. The applicator is aligned to apply the composition to a location within the imaged area of skin. The device analyzes the image data and selectively applies the composition to the location when a reflectance value of the area of skin is (i) less than a reflectance value of the selected tone, and (ii) greater than a reflectance value of the location. The reflectance value of the selected tone is generated based on image data corresponding to a region of skin adjacent to the area of skin.

15 Claims, 7 Drawing Sheets

(58) Field of Classification Search
CPC ......... A61B 5/103; A61B 5/441; A61B 5/442; A61M 2205/3306; A61M 2210/04; A61M 35/003; A61Q 1/00; A61Q 1/02; A61Q 1/025; A61Q 1/04; A61Q 1/06; A61Q 1/08; A61Q 1/10; A61Q 1/12; A61Q 1/14; A61Q 19/00; A61Q 19/02; A61Q 19/04; A61Q 19/08
See application file for complete search history.

(56) References Cited

U.S. PATENT DOCUMENTS

| | | | | |
|---|---|---|---|---|
| 8,007,062 | B2 | 8/2011 | Edgar et al. | |
| 8,027,505 | B2 | 9/2011 | Edgar et al. | |
| 8,103,061 | B2 | 1/2012 | Payonk et al. | |
| 8,878,905 | B2 | 11/2014 | Fisker et al. | |
| 8,915,562 | B2 * | 12/2014 | Edgar | G06V 10/60 347/1 |
| 8,942,775 | B2 | 1/2015 | Edgar et al. | |
| 9,020,184 | B2 * | 4/2015 | Edgar | A61B 5/448 382/199 |
| 9,096,882 | B2 | 8/2015 | Meyer et al. | |
| 9,247,802 | B2 | 2/2016 | Edgar et al. | |
| 9,449,382 | B2 | 9/2016 | Edgar et al. | |
| 9,462,872 | B2 | 10/2016 | Edgar | |
| 9,522,101 | B2 | 12/2016 | Rabe et al. | |
| 9,949,552 | B2 | 4/2018 | Rabe et al. | |
| 10,010,155 | B2 | 7/2018 | Ajiki et al. | |
| 10,092,082 | B2 | 10/2018 | Edgar et al. | |
| 10,242,278 | B2 | 3/2019 | Makkapti et al. | |
| 10,405,795 | B1 | 9/2019 | Osorio et al. | |
| 10,486,174 | B2 | 11/2019 | Edgar et al. | |
| 10,553,006 | B2 | 2/2020 | Iglchart et al. | |
| 10,614,921 | B2 | 4/2020 | Shen et al. | |
| 10,646,472 | B2 | 5/2020 | Taratula et al. | |
| 10,796,431 | B2 * | 10/2020 | Iglehart | G01J 3/10 |
| 11,039,886 | B2 | 6/2021 | Verghese et al. | |
| 11,090,474 | B2 | 8/2021 | Edgar | |
| 11,110,257 | B2 | 9/2021 | Edgar | |
| 11,291,287 | B2 | 4/2022 | Samain et al. | |
| 11,535,603 | B1 | 12/2022 | DeWitt | |
| 12,011,561 | B2 | 6/2024 | Edgar et al. | |
| 12,472,336 | B2 | 11/2025 | Edgar et al. | |
| 2003/0100837 | A1 | 5/2003 | Lys et al. | |
| 2004/0078278 | A1 | 4/2004 | Dauga et al. | |
| 2004/0186373 | A1 | 9/2004 | Dunfield et al. | |
| 2005/0010102 | A1 | 1/2005 | Marchesini et al. | |
| 2007/0035815 | A1 | 2/2007 | Edgar et al. | |
| 2008/0192999 | A1 * | 8/2008 | Edgar | H04N 1/622 382/128 |
| 2009/0025747 | A1 | 1/2009 | Edgar et al. | |
| 2011/0224163 | A1 | 9/2011 | Nakajo et al. | |
| 2013/0302078 | A1 | 11/2013 | Edgar | |
| 2014/0323873 | A1 | 10/2014 | Cummins et al. | |
| 2014/0333744 | A1 | 11/2014 | Baym et al. | |
| 2015/0254816 | A1 | 9/2015 | Carlson et al. | |
| 2015/0360016 | A1 | 12/2015 | Rabe et al. | |
| 2016/0000209 | A1 | 1/2016 | Yamanashi et al. | |
| 2016/0107133 | A1 | 4/2016 | Sugino et al. | |
| 2017/0078584 | A1 | 3/2017 | Won | |
| 2017/0156994 | A1 | 6/2017 | Lingoes et al. | |
| 2017/0256084 | A1 | 9/2017 | Iglehart et al. | |
| 2017/0340267 | A1 | 11/2017 | Shen et al. | |
| 2018/0126342 | A1 | 5/2018 | Kent | |
| 2018/0204353 | A1 | 7/2018 | Yoshida | |
| 2018/0318186 | A1 | 11/2018 | Chabrillangeas et al. | |
| 2019/0080451 | A1 | 3/2019 | Iglehart et al. | |
| 2019/0239752 | A1 | 8/2019 | Dumitrescu et al. | |
| 2020/0107715 | A1 | 4/2020 | Dana et al. | |
| 2020/0206487 | A1 | 7/2020 | Edgar | |
| 2021/0046296 | A1 | 2/2021 | Binner et al. | |
| 2021/0402208 | A1 | 12/2021 | Edgar | |
| 2022/0054811 | A1 | 2/2022 | Edgar | |
| 2022/0237811 | A1 | 7/2022 | Cai et al. | |
| 2022/0401514 | A1 | 12/2022 | Such | |

FOREIGN PATENT DOCUMENTS

| | | | |
|---|---|---|---|
| CN | 101925816 | | 12/2010 |
| CN | 103052376 | A | 4/2013 |
| CN | 103180872 | A | 6/2013 |
| CN | 106457847 | | 2/2017 |
| CN | 106572737 | | 4/2017 |
| CN | 106999116 | | 8/2017 |
| CN | 107847720 | | 3/2018 |
| CN | 108135346 | A | 6/2018 |
| CN | 108354587 | | 8/2018 |
| CN | 110167954 | A | 8/2019 |
| CN | 110636828 | A | 12/2019 |
| CN | 110114029 | | 10/2022 |
| JP | 2000-129185 | | 5/2000 |
| JP | 2004-283578 | | 10/2004 |
| JP | 2009-5042772 | | 2/2009 |
| JP | 2011-080915 | A | 4/2011 |
| JP | 2012-515062 | | 7/2012 |
| JP | 2012-530267 | | 11/2012 |
| JP | 2017-113140 | | 6/2017 |
| JP | 2017-525657 | | 9/2017 |
| JP | 2018-513875 | | 5/2018 |
| JP | 2019-007895 | A | 1/2019 |
| JP | 2019-026599 | | 2/2019 |
| JP | 2019-518573 | A | 7/2019 |
| KR | 10-2010-0117038 | | 11/2010 |
| KR | 10-2018-0094012 | | 8/2018 |
| RU | 2 709 930 | C1 | 12/2019 |
| RU | 2018135258 | | 9/2020 |
| WO | WO 2007/022095 | A1 | 2/2007 |
| WO | WO 2007106501 | | 9/2007 |
| WO | WO 2008150928 | | 12/2008 |
| WO | 2010/004565 | A2 | 1/2010 |
| WO | WO 2010083405 | | 7/2010 |
| WO | 2010/145669 | | 12/2010 |
| WO | WO 2012001289 | | 1/2012 |
| WO | WO 2012/025477 | | 3/2012 |
| WO | 2012/103048 | A2 | 8/2012 |
| WO | WO 2015103420 | | 7/2015 |
| WO | 2015/161009 | A1 | 10/2015 |
| WO | 2015/191824 | | 12/2015 |
| WO | WO 2016191217 | | 12/2016 |
| WO | WO 2017035328 | | 3/2017 |
| WO | WO 2017/056980 | | 4/2017 |
| WO | WO 2017/181293 | A1 | 10/2017 |
| WO | WO 2018/057912 | | 3/2018 |
| WO | WO 2018/231915 | | 12/2018 |
| WO | WO 2020/139890 | A1 | 7/2020 |
| WO | WO 2020136103 | | 7/2020 |

OTHER PUBLICATIONS

International Preliminary Report on Patentability issued Feb. 7, 2023 in corresponding International Application No. PCT/US2021/071079.

International Search Report and Written Opinion mailed on Mar. 23, 2022 in corresponding International Application No. PCT/US2021/061226.

Alcón et al, "Automatic Imaging System with Decision Support for Inspection of Pigmented Skin Lesions and Melanoma Diagnosis," IEEE Journal of Selected Topics in Signal Processing, vol. 3, No. 1, Feb. 2009, pp. 14-25.

Search Report mailed on Feb. 18, 2025 in counterpart Russian patent application No. 2023 119 003.

Office Action mailed on Feb. 18, 2025 in counterpart Russian patent application No. 2023 119 003 and its English translation of relevant parts of the Office Action.

* cited by examiner

DEVICE AND METHOD FOR CONTINUOUS EVEN APPLICATION OF COMPOSITION TO SKIN

PRIORITY CLAIM

The present application claims priority to U.S. Provisional Application Ser. No. 63/199,354 entitled "Device and Method for Continuous Even Application of Composition to Skin," filed Dec. 21, 2020, the entire contents of which is hereby incorporated by reference herein.

FIELD OF INVENTION

The present invention relates to devices and methods for selectively applying a composition onto a treatment surface, such as a keratinous surface, (e.g., the skin, hair, or nails), or enamel (e.g., teeth) of a user. More specifically, the invention relates to devices and methods for selectively applying a topical composition to reduce appearance of undesirable skin artifacts and enhance the aesthetic appearance of skin.

BACKGROUND

Traditional cosmetic application often requires manual application that does not discriminate between an area of the skin whose appearance is in need of modification and those that do not require any modification. For example, people seeking to cover or alter the appearance of features on the skin (e.g., acne, scars, age spots, etc.) typically apply a layer of a foundational base of make-up across the entire surface of the skin to create a uniform appearance that may result in an unnatural, flat, painted, or caked-on appearance. Applying cosmetics indiscriminately over large areas of skin also wastes material as the cosmetic is also applied to portions of the skin that may need little or no modification. However, it is also difficult to manually apply cosmetics to only those portions of skin in need of modification with sufficient precision and control without creating an unnatural or splotchy appearance. In addition, manual application of a continuous layer of cosmetic may impart a film over large portions of skin, which may cause a displeasing, less natural feel for the skin. Such a film over large portions of skin may also decrease breathability of the skin and increase exposure of the skin to the cosmetic material, which can increase the surface area of skin exposed to potential allergens and therefore, increase the risk that a user may have undesired or allergic reactions to the cosmetic material.

SUMMARY OF THE INVENTION

One exemplary embodiment of the present invention is directed to a method for selectively applying a composition to skin of a user. The method comprises obtaining, by a detector arrangement, image data corresponding to an image of an area of skin, the area of skin imaged by the detector arrangement. The method also comprises analyzing, by a processing arrangement, the image data to generate a reflectance value of the area of skin and a reflectance value of a location within the area of skin. The method further comprises comparing, by the processing arrangement, the reflectance value of the area of skin to: (i) a reflectance value of a selected tone, and (ii) the reflectance value of the location. The reflectance value of the selected tone is generated based on image data corresponding to a region of skin adjacent to the area of skin. The method further comprises selectively applying, by an applicator arrangement, the composition to the location when the reflectance value of the area of skin is (i) less than the reflectance value of the selected tone, and (ii) greater than the reflectance value of the location.

In another aspect of the present application, a handheld device for selectively applying a composition to skin of a user is provided. The device comprises a detector arrangement obtaining image data corresponding to an image of an area of skin. The device also comprises an applicator arrangement applying the composition to the skin, wherein the applicator arrangement is aligned to apply the composition to a location within the area of skin. The device further comprises a memory storage device storing past image data corresponding to an area of skin previously imaged by the detector arrangement. The device further comprises a processor and a non-transitory computer readable storage medium including a set of instructions executable by the processor, the set of instructions operable to analyze the image data to generate a reflectance value of the area of skin and a reflectance value of the location within the area of skin, compare the reflectance value of the area of skin to: (i) a reflectance value of a selected tone, and (ii) the reflectance value of the location, wherein the reflectance value of the selected tone is generated based on image data corresponding to a region of skin adjacent to the area of skin, and direct the applicator arrangement to selectively apply the composition to the location when the reflectance value of the area of skin is less than the reflectance value of the selected tone, and greater than the reflectance value of the location.

These and other aspects of the invention will become apparent to those skilled in the art after a reading of the following detailed description of the invention, including the figures and appended claims.

DESCRIPTION

Figure 1:
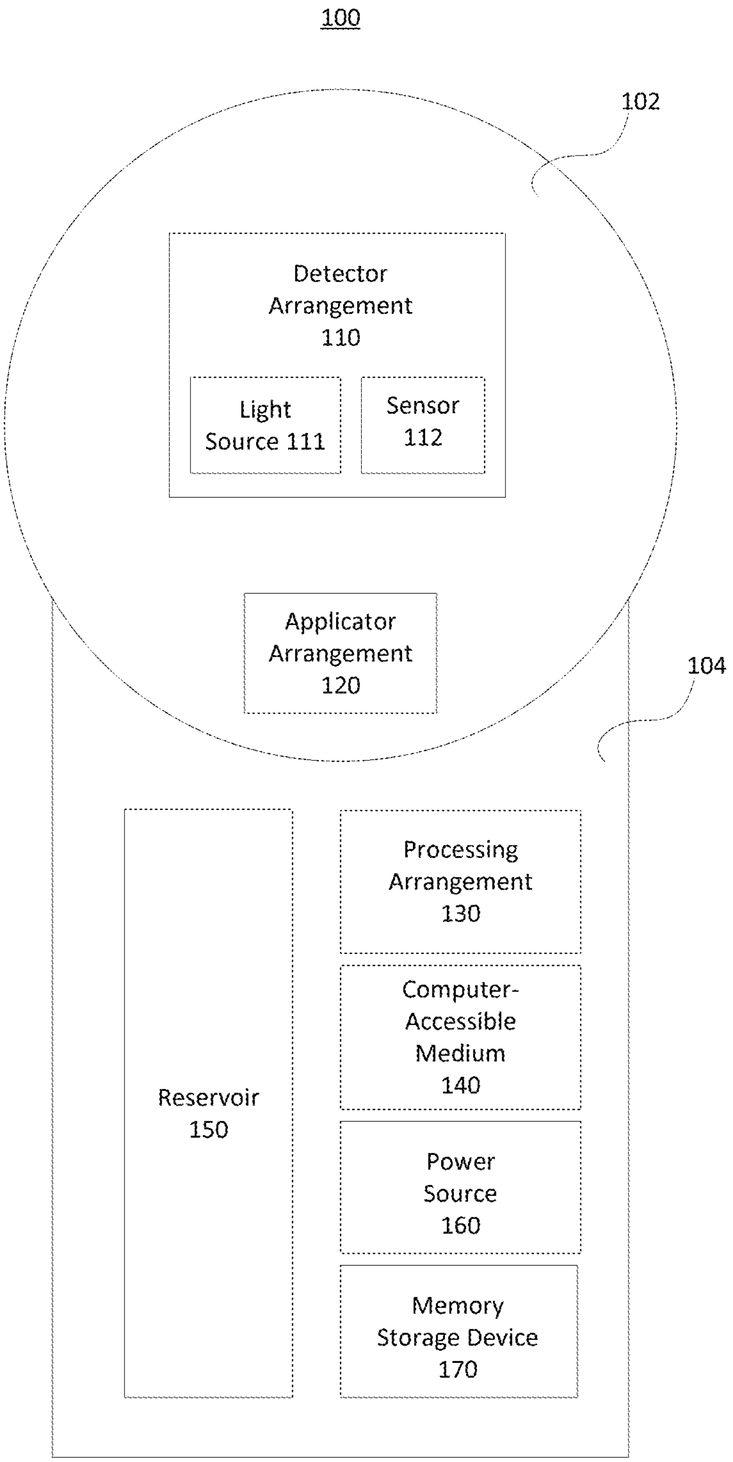
FIG. 1 shows a block diagram of an exemplary device for selectively applying a composition to the skin of a user, according to an exemplary embodiment of the present application.

The term "suitable for topical application" or "suitable for topical administration" as used herein refers to those ingredients and/or treatments that are suitable for use on the skin, in particular, the skin of a human, without undue toxicity, incompatibility, instability, irritation, allergic response, unsightly visual appearance or the like.

The term "frexel" as used herein refers to a small pixel-like region of skin, which may correspond to a single large pixel or a small number of pixels in a digitally obtained image of the corresponding portion of skin. For example, a frexel may correspond to a skin area having an average diameter from about 1/32 to about 1/4 inch.

The term "about" as used herein has its conventional meaning. In particular embodiments, where in relation to a numerical value, it may be interpreted to mean the numerical value±10%, or ±5%, or ±2%, or ±1%, or ±0.5%, or ±0.1%. In other embodiments, the precise value is meant, i.e., by leaving out the word "about."

The term "middle spatial frequencies" as used herein is explained further below. For example, image data corresponding to an image of the skin can capture light reflectances extending over a range of spatial frequencies, which measures the level of detail present in an image over a distance across the skin observed by a detector (e.g., a camera) that generates the image data. Spatial frequency may be measured by the number of periodic features, e.g., described as a periodic sine-wave pattern corresponding to cycles of alternating dark and light stripe patterns, within an image over a distance across the skin observed by the detector. The spatial frequency of an image may be calibrated and/or normalized based on a distance from which the skin is imaged by the detector. It is noted that spatial frequency, as used herein, does not measure a wavelength or color of light, but instead refers to a spatial wavelength of the structure of the details of the skin captured by the detector in the image. Data corresponding to an image in a spatial domain (e.g., in the form of pixels or frexel) can be processed by a computer processor using a Fourier transform function to obtain data for the image in the spatial frequency domain. This spatial frequency domain relates to an optical resolution of the image captured, which is distinct from a wavelength or color of light. As would be understood by those skilled in the art, the spatial frequency components of the image may generally be separated into three different categories, including (1) high spatial frequencies, (2) middle spatial frequencies, and (3) low spatial frequencies, using any suitable methods for image analysis, e.g., Fourier transform, filtering, etc. As would be understood by those skilled in the art, spatial frequency components having high spatial frequencies correspond to light reflectance in the image that contribute to the appearance of sharp edges and small details within the image. For example, for an image of skin, the spatial frequency components having high spatial frequencies correspond to features that appear to be small, natural variations in the skin, such as those derived from the genetic code of the person, e.g., pores, hair, follicles, cells, iris of the eye, etc. Low spatial frequencies correspond to light reflectances in the image that contribute to the broad visual appearance such as, for example, the color of larger features such as, for example, the nose, cheeks, etc. The remaining spatial frequency components between the low and spectral frequencies are referred to as the middle spatial frequencies.

The range of middle spatial frequencies may be determined relative to the image captured. For example, the range of middle spatial frequencies for an area of facial skin may be different from the range of middle spatial frequencies for an area of the skin on a leg. The range of middle spatial frequencies may also depend on the underlying skin tone of the skin imaged. In one example, the middle spatial frequencies for human skin can range from about 0.03 cycles/mm to about 1.5 cycles/mm, or more specifically from about 0.05 cycles/mm to about 1.0 cycles/mm and, even more specifically, from about 0.07 cycles/mm to about 0.5 cycles/mm.

The present application provides a device and method for selectively applying a composition to a treatment surface. It is contemplated that the composition may be applied to any suitable treatment surface, such as, an interface between a biological surface and the external environment (e.g., air), in particular, a topical surface. Suitable biological surfaces may include keratinous surfaces (such as, but not limited to, surfaces of the skin, hair, and/or nails), and enameled surfaces (e.g., a surface of a tooth). Preferably, the treatment surface is that of a mammal or a human. Although exemplary embodiments are discussed herein relating to the skin, it is contemplated that the device and method of the present application may be used to selectively apply any suitable composition, in particular, a topical composition to a treatment surface. More particularly, the present application provides a device and method for selectively applying a topical composition to the skin of a face of the user to address skin artifacts, e.g., scars, wrinkles, blemishes, freckles, sun damage, age spots, etc., whose appearance the user wishes to minimize or eliminate to improve an overall aesthetic appearance of the face of the user. The device of the present application analyzes an image of an area of skin to identify locations to which the composition should be applied to alter the visual appearance of the skin artifacts. The composition may be a cosmetic composition and/or a skin treatment composition for improving the appearance and/or health of the skin.

FIG. 1 shows a block diagram of an exemplary device 100 for applying a topical composition to the skin. The device 100 of this embodiment is sized and shaped to be a handheld device designed to be held within a palm of a user's hand. The device 100 according to this embodiment comprises a head portion 102 and a handle portion 104. In one embodiment, the head portion 102 of the device 100 is sized and shaped to be held over an area of skin, for example, an area of skin on the face of the user. The handle portion 104 of the device 100 has an elongated shape defining a cavity for housing components therein. In some embodiments, the handle portion 104 is sized and shaped to be held within the palm of the user's hand. In other embodiments, the handle portion 104 is sized and shaped to be held by the fingertips of the user's hand.

The head portion 102 of the device 100 according to this embodiment comprises a detector arrangement 110 obtaining image data corresponding to an image of an area of skin. The head portion 102 of this embodiment also comprises an applicator arrangement 120 selectively applying the composition to portions of the skin as directed by a processing arrangement 130 based on image data from the detector arrangement 110. In some embodiments, the detector arrangement 110 and the applicator arrangement 120 are part of an inset portion (not shown) of the head portion 102 such that when the head portion 102 is placed over an area of skin to be treated, the inset portion is not in contact with the skin.

The detector arrangement 110 comprises at least one light source 111 delivering light (e.g., visible light) to the area of skin, and at least one sensor 112 detecting light reflected from the area of the skin. The light source(s) 111 may comprise any suitable light emitting device for illuminating the area of skin, for example, one or more LEDs. The light source(s) 111 are selected and arranged to provide an amount of illumination over the area of skin sufficient to detect and/or measure reflectance of light by the skin. Preferably, the light source(s) 111, collectively, provide a substantially uniform distribution of light over the area of skin. In one exemplary embodiment, the light source(s) 111 comprise at least one light emitting device for providing a green light. In a specific example, the light source(s) 111 comprise at least one green LED. The sensor 112 may comprise any suitable components for detecting reflectance of light from the skin. For example, the sensor 112 may be sensitive to light in one or more wavelengths. Suitable sensors 112 may include, for example, photographic or video cameras (which may include different types of camera lenses), photodiodes and/or phototransistors as would be understood by those skilled in the art. The sensor(s) 112 of the detector arrangement 110 may be an RGB camera which can detect light in red, green and/or blue channels of the camera.

The detector arrangement 110, including the light source(s) 111 and sensor(s) 112, is operably connected to a processing arrangement 130 to execute instructions stored on a computer-accessible medium 140. The processing arrangement 130 in this embodiment controls the light source(s) 111 and receives and analyzes imaging data received from the sensor(s) 112. It is contemplated that the processing arrangement 130 and the computer-accessible medium 140 may be positioned anywhere within or external to the device 100. In one embodiment, as shown in FIG. 1, the processing arrangement 130 and the computer-accessible medium 140 are located within the handle portion 104. The processing arrangement 130 in this embodiment also controls the applicator arrangement 120 to selectively apply the composition to desired frexels. The processing arrangement 130 may be, e.g., entirely or a part of, or include, but is not limited to, a computer/processor that can include, e.g., one or more microprocessors, and use instructions stored on a computer-accessible medium 140 (e.g., memory storage device). The computer-accessible medium 140 may, for example, be a non-transitory computer-accessible medium containing executable instructions therein. The device 100 may further include a memory storage device 170 for storing past image data correspond to images of a plurality of areas of skin previously imaged by the detector arrangement 110. The computer-accessible medium 140 and/or the memory storage device 170 may be any type circuit or storage device for storing digital data, such as, for example, ROM, PROM, EEPROM, DRAM, SDRAM, DDR/2 SDRAM, EDO/FPMS, RLDRAM, SRAM, flash memory (e.g., NAND/NOR), and PSRAM.

The applicator arrangement 120 according to this embodiment comprises at least one suitable application device for depositing a topical composition (e.g., a cosmetic composition and/or a skin treatment composition) onto frexels. An exemplary topical composition application device in this embodiment includes, for example, a sprayer (e.g., an electronic sprayer or airbrush sprayer), a drop control device, or any other suitable application device for applying a composition in small drops to desired locations as would be understood by those skilled in the art. In one exemplary embodiment, the applicator arrangement 120 comprises a nozzle for depositing a liquid or viscous composition in the form of a pressurized mist onto the skin to form a thin layer of coverage at a desired location. The thin layer may be in the form of a continuous film or a discontinuous spread of the composition across the skin. The nozzle may be any suitable device for depositing a thin layer of the composition onto aimed locations on the skin. In one exemplary embodiment, the nozzle may comprise dual chambers with a first chamber holding the liquid or viscous composition and a second chamber containing a propellant (e.g., compressed air or nitrogen gas) applying a pressure to, but not mixed with the composition when a pulse of the composition is dispensed to a frexel. In another example, the nozzle comprises a first chamber holding the liquid or viscous composition and a second chamber containing a propellant to be mixed with the composition when the composition is dispensed to a desired location. In some embodiments, the nozzle may comprise a venturi nozzle. Although exemplary embodiments of the nozzle are described above, it is contemplated that the device of the present application may include any suitable nozzle for dispensing droplets of the composition under pressure as would be understood by those skilled in the art. In one exemplary embodiment, the applicator arrangement 120 is configured to deposit the topical composition in a plurality of pulses, each pulse depositing a fixed amount of the topical composition to the skin.

The applicator arrangement 120 is operably connected to a reservoir 150 containing a topical composition to be applied to the skin, such that the composition within the reservoir 150 can be transferred from the reservoir 150 to the applicator arrangement 120 for deposition onto the skin. In particular, the applicator arrangement 120 is fluidly connected by a series of conduits, valves, and/or pressure sources to the reservoir 150. It is contemplated that the reservoir 150 may be housed anywhere within the device 100. In one exemplary embodiment, as shown in FIG. 1, the reservoir 150 is housed within the handle portion 104 of the device 100. The composition within the reservoir 150 is transferred from the reservoir 150 to the applicator arrangement 120 for deposition of the composition. In some embodiments, the reservoir 150 is a removeable container that can be replaced upon exhaustion of the contents therein. For example, the reservoir 150 may be a pressurized canister containing the composition to be applied to the skin therein.

The composition to be applied to the skin may be any composition suitable for topical application to the skin of a face. The composition to be applied to the skin may comprise, for example, any suitable cosmetic ingredients for modifying an appearance of the skin, such as, for example, an opaque substance, a tinted cosmetic, or any other suitable compositions for enhancing the appearance of skin. The composition may also comprise ingredients such as a moisturizer for hydration, a carrier, or a benefit agent (e.g., a beneficial compound/composition/extract or an active ingredient) for treating and/or ameliorating a skin condition, e.g., acne, hyperpigmentation, eczema, hives, vitiligo, psoriasis, rosacea, warts, shingles, cold sore, pigmentation and tone, redness/oxidative skin stress, wrinkles, brightening, sagging/elasticity, etc. Exemplary embodiments of benefit agents that may be incorporated into the composition are further described below.

A non-limiting list of useful hydrating active benefit agents includes hyaluronic acid, and humectants. The hyaluronic acid may be linear, cross-linked, or a mixture of linear and cross-linked hyaluronic acid. It may be in a salt form, such as sodium hyaluronate. A humectant is a compound intended to increase the water content of the top layers of skin (e.g., hygroscopic compounds). Examples of suitable humectants include, but are not limited to, glycerin, sorbitol or trehalose or a salt or ester thereof.

A non-limiting list of useful benefit agents for acne includes benzoyl peroxide, retinoids including retinol, retinal, retinoic acid, retinyl acetate, and retinyl palmitate, hydroxy acids include, but are not limited, to glycolic acid, lactic acid, malic acid, salicylic acid, citric acid, and tartaric acid, sulfur, Zinc PCA (Zinc Pyrrolidone carboxylic acid), Allantoin (5-ureidohydantoin), Rosemary, 4-hexylresorcinol, N-acetyl glucosamine, gluconolactone, niacinamide, azelaic acid, and resveratrol.

A non-limiting list of useful pigmentation active benefit agents includes resorcinols, such as niacinamide, 4-hexyl resorcinol, curcuminoids (such as Sabiwhite (Tetrahydrocurcumin), phytic acid, resveratrol, soybean glycine soja oil, gluconolactone, azelaic acid, and retinoids including retinol, retinal, retinoic acid, retinyl acetate, and retinyl palmitate, enzymes such as laccase, tyrosinase inhibitors, melanin-degradation agents, melanosome transfer inhibiting agents including PAR-2 antagonists, exfoliants, sunscreens, retinoids, antioxidants, Tranexamic acid, tranexamic acid cetyl ester hydrochloride, skin bleaching agents, linoleic acid, adenosine monophosphate disodium salt, Chamomilla extract, allantoin, opacifiers, talcs and silicas, zinc salts, and the like. Examples of suitable tyrosinase inhibitors include but, are not limited to, Vitamin C and its derivatives, Vitamin E and its derivatives, Kojic Acid, Arbutin, resorcinols, hydroquinone, Flavones e.g., Licorice flavanoids, Licorice root extract, Mulberry root extract, Dioscorea Coposita root extract, Saxifraga extract and the like, Ellagic acid, Salicylates and derivatives, Glucosamine and derivatives, Fullerene, Hinokitiol, Dioic acid, Acetyl glucosamine, 5,5'-dipropyl-biphenyl-2,2'-diol (Magnolignan), 4-(4-hydroxyphenyl)-2-butanol (4-HPB), combinations of two or more thereof, and the like. Examples of vitamin C derivatives include, but are not limited to, ascorbic acid and salts, Ascorbic Acid-2-Glucoside, sodium ascorbyl phosphate, magnesium ascorbyl phosphate, and natural extract enriched in vitamin C. Examples of vitamin E derivatives include, but are not limited to, alpha-tocopherol, beta, tocopherol, gamma-tocopherol, delta-tocopherol, alpha-tocotrienol, beta-tocotrienol, gamma-tocotrienol, delta-tocotrienol and mixtures thereof, tocopherol acetate, tocopherol phosphate and natural extracts enriched in vitamin E derivatives. Examples of resorcinol derivatives include, but are not limited to, resorcinol, 4-substituted resorcinols like 4-alkylresorcinols such as 4-butyresorcinol (rucinol), 4-hexylresorcinol, phenylethyl resorcinol, 1-(2,4-dihydroxyphenyl)-3-(2,4-dimethoxy-3-methylphenyl)-Propane and the like and natural extracts enriched in resorcinols. Examples of salicylates include, but are not limited to, 4-methoxy potassium salicylate, salicylic acid, acetylsalicylic acid, 4-methoxysalicylic acid and their salts. In certain preferred embodiments, the tyrosinase inhibitors include a 4-substituted resorcinol, a vitamin C derivative, or a vitamin E derivative A non-limiting list of useful redness/antioxidant active benefit agents includes water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, propolis and extracts of feverfew. By "extracts of feverfew," it is meant extracts of the plant "Tanacetum parthenium," One particularly suitable feverfew extract is commercially available as about 20% active feverfew.

A non-limiting list of useful wrinkle active benefit agents includes N-acetyl glucosamine, 2-dimethylaminoethanol, copper salts such as copper chloride, peptides like argireline, syn-ake and those containing copper, coenzyme Q10, dill, blackberry, princess tree, picia anomala, and chicory, resorcinols, such as 4-hexyl resorcinol, curcuminoids and retinoids including retinol, retinal, retinoic acid, retinyl acetate, and retinyl palmitate, hydroxy acids include, but are not limited, to glycolic acid, lactic acid, malic acid, salicylic acid, citric acid, and tartaric acid.

A non-limiting list of useful brightening active benefit agents includes Vitamin C and its derivatives such as Ascorbic Acid 2-Glucoside, alpha-hydroxy acids such as lactic acid, glycolic acid, malic acid, tartaric acid, citric acid, or any combination of any of the foregoing, beta-hydroxy acids such as salicylic acid, polyhydroxy acids such as lactobionic acid and gluconic acid.

A non-limiting list of useful benefit agents for sagging skin includes blackberry extracts, cotinus extracts, feverfew extracts, extracts of Phyllanthus niruri and bimetal complexes having copper and/or zinc constituents. The bimetal complex having copper and/or zinc constituents may be, for example, copper-zinc citrate, copper-zinc oxalate, copper-zinc tartarate, copper-zinc malate, copper-zinc succinate, copper-zinc malonate, copper-zinc maleate, copper-zinc aspartate, copper-zinc glutamate, copper-zinc glutarate, copper-zinc fumarate, copper-zinc glucarate, copper-zinc polyacrylic acid, copper-zinc adipate, copper-zinc pimelate, copper-zinc suberate, copper-zinc azealate, copper-zinc sebacate, copper-zinc dodecanoate, or combinations thereof.

Additional skin benefit agents or actives may include those actives listed in the following paragraphs. While some of these actives may have been listed above, they are included below to ensure a more robust listing.

Examples of suitable additional benefit agents include: skin lightening agents, darkening agents, anti-aging agents, tropoelastin promoters, collagen promoters, anti-acne agents, shine control agents, anti-microbial agents such as anti-yeast agents, anti-fungal, and anti-bacterial agents, anti-inflammatory agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, hair growth enhancing agents, hair growth delaying agents, firming agents, hydration boosters, efficacy boosters, anti-callous agents, agents for skin conditioning, anti-cellulite agents, fluorides, teeth whitening agents, anti-plaque agents, and plaque-dissolving agents, odor-control agents such as odor masking or pH-changing agents, and the like. Examples of various suitable additional cosmetically acceptable actives include UV filters such as but not limited to avobenzone (Parsol 1789), bisdisulizole disodium (Neo Heliopan AP), diethylamino hydroxybenzoyl hexyl benzoate (Uvinul A Plus), ecamsule (Mexoryl SX), methyl anthranilate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), padimate O (Escalol 507), phenylbenzimidazole sulfonic acid (Ensulizole), polysilicone-15 (Parsol SLX), trolamine salicylate, Bemotrizinol (Tinosorb S), benzophenones 1-12, dioxybenzone, drometrizole trisiloxane (Mexoryl XL), iscotrizinol (Uvasorb HEB), octocrylene, oxybenzone (Eusolex 4360), sulisobenzone, bisoctrizole (Tinosorb M), titanium dioxide, zinc oxide, carotenoids, free radical scavengers, spin traps, retinoids and retinoid precursors such as retinol, retinoic acid and retinyl palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper such as Cu:Gly-His-Lys, coenzyme Q10, amino acids such a proline, vitamins, lactobionic acid, acetyl-coenzyme A, niacin, riboflavin, thiamin, ribose, electron transporters such as NADH and FADH2, and other botanical extracts such as oat, aloe vera, Feverfew, Soy, Shiitake mushroom extracts, and derivatives and mixtures thereof.

Examples of suitable skin lightening benefit agents include, but are not limited to, tyrosinase inhibitors, melanin-degradation agents, melanosome transfer inhibiting agents including PAR-2 antagonists, exfoliants, sunscreens, retinoids, antioxidants, Tranexamic acid, tranexamic acid cetyl ester hydrochloride, skin bleaching agents, linoleic acid, adenosine monophosphate disodium salt, Chamomilla extract, allantoin, opacifiers, talcs and silicas, zinc salts, and the like.

Examples of suitable tyrosinase inhibitors include but, are not limited to, Vitamin C and its derivatives, Vitamin E and its derivatives, Kojic Acid, Arbutin, resorcinols, hydroquinone, Flavones e.g. Licorice flavanoids, Licorice root extract, Mulberry root extract, Dioscorea Coposita root extract, Saxifraga extract and the like, Ellagic acid, Salicylates and derivatives, Glucosamine and derivatives, Fullerene, Hinokitiol, Dioic acid, Acetyl glucosamine, 5,5'-dipropyl-biphenyl-2,2'-diol (Magnolignan), 4-(4-hydroxyphenyl)-2-butanol (4-HPB), combinations of two or more thereof, and the like. Examples of vitamin C derivatives include, but are not limited to, ascorbic acid and salts, Ascorbic Acid-2-Glucoside, sodium ascorbyl phosphate, magnesium ascorbyl phosphate, and natural extract enriched in vitamin C. Examples of vitamin E derivatives include, but are not limited to, alpha-tocopherol, beta, tocopherol, gamma-tocopherol, delta-tocopherol, alpha-tocotrienol, beta-tocotrienol, gamma-tocotrienol, delta-tocotrienol and mixtures thereof, tocopherol acetate, tocopherol phosphate and natural extracts enriched in vitamin E derivatives. Examples of resorcinol derivatives include, but are not limited to, resorcinol, 4-substituted resorcinols like 4-alkylresorcinols such as 4-butyresorcinol (rucinol), 4-hexylresorcinol (Synovea HR, Sytheon), phenylethyl resorcinol (Symwhite, Symrise), 1-(2,4-dihydroxyphenyl)-3-(2,4-dimethoxy-3-methylphenyl)-Propane (nivitol, Unigen) and the like and natural extracts enriched in resorcinols. Examples of salicylates include, but are not limited to, 4-methoxy potassium salicylate, salicylic acid, acetylsalicylic acid, 4-methoxysalicylic acid and their salts. In certain preferred embodiments, the tyrosinase inhibitors include a 4-substituted resorcinol, a vitamin C derivative, or a vitamin E derivative. In more preferred embodiments, the tyrosinase inhibitor comprises Phenylethyl resorcinol, 4-hexyl resorcinol, or ascorbyl-2-glucoside.

Examples of suitable melanin-degradation agents include, but are not limited to, peroxides and enzymes such as peroxidases and ligninases. In certain preferred embodiments, the melanin-inhibiting agents include a peroxide or a ligninase.

Examples of suitable melanosome transfer inhibiting agents including PAR-2 antagonists such as soy trypsin inhibitor or Bowman-Birk Inhibitor, Vitamin B3 and derivatives such as Niacinamide, Essential soy, Whole Soy, Soy extract. In certain preferred embodiments, the melanosome transfer inhibiting agents includes a soy extract or niacinamide.

Examples of exfoliants include, but are not limited to, alpha-hydroxy acids such as lactic acid, glycolic acid, malic acid, tartaric acid, citric acid, or any combination of any of the foregoing, beta-hydroxy acids such as salicylic acid, polyhydroxy acids such as lactobionic acid and gluconic acid, and mechanical exfoliation such as microdermabrasion. In certain preferred embodiments, the exfoliant include glycolic acid or salicylic acid.

Examples of sunscreens include, but are not limited to, avobenzone (Parsol 1789), bisdisulizole disodium (Neo Heliopan AP), diethylamino hydroxybenzoyl hexyl benzoate (Uvinul A Plus), ecamsule (Mexoryl SX), methyl anthranilate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), padimate O (Escalol 507), phenylbenzimidazole sulfonic acid (Ensulizole), polysilicone-15 (Parsol SLX), trolamine salicylate, Bemotrizinol (Tinosorb S), benzophenones 1-12, dioxybenzone, drometrizole trisiloxane (Mexoryl XL), iscotrizinol (Uvasorb HEB), octocrylene, oxybenzone (Eusolex 4360), sulisobenzone, bisoctrizole (Tinosorb M), titanium dioxide, zinc oxide, and the like.

Examples of retinoids include, but are not limited to, retinol (Vitamin A alcohol), retinal (Vitamin A aldehyde), retinyl acetate, retinyl propionate, retinyl linoleate, retinoic acid, retinyl palmitate, isotretinoin, tazarotene, bexarotene, Adapalene, combinations of two or more thereof and the like. In certain preferred embodiments, the retinoid is selected from the group consisting of retinol, retinal, retinyl acetate, retinyl propionate, retinyl linoleate, and combinations of two or more thereof. In certain more preferred embodiments, the retinoid is retinol.

Examples of antioxidants include, but are not limited to, water-soluble antioxidants such as sulfhydryl compounds and their derivatives (e.g., sodium metabisulfite and N-acetyl-cysteine, glutathione), lipoic acid and dihydrolipoic acid, stilbenoids such as resveratrol and derivatives, lactoferrin, iron and copper chelators and ascorbic acid and ascorbic acid derivatives (e.g., ascobyl-2-glucoside, ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinones. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, black tea, white tea, pine bark, feverfew, parthenolide-free feverfew, oat extracts, blackberry extract, cotinus extract, soy extract, pomelo extract, wheat germ extract, Hesperedin, Grape extract, Portulaca extract, Licochalcone, chalcone, 2,2'-dihydroxy chalcone, Primula extract, propolis, and the like.

In some preferred embodiments, useful benefit agents for acne include, but are not limited, salicylic acid, Zinc PCA (Zinc Pyrrolidone carboxylic acid), Allantoin (5-ureidohydantoin), Rosemary, 4-hexylresorcinol, N-acetyl glucosamine, gluconolactone, niacinamide, azelaic acid, and resveratrol.

In some preferred embodiments, a list of useful pigmentation active benefit agents includes tetrahydrocurcumin, phytic acid, resveratrol, soybean glycine soja oil, gluconolactone, laccase, 4-hexyl resorcinol, N-acetyl glucosamine, gluconolactone, niacinamide, azelaic acid, and resveratrol.

In some preferred embodiments, a list of useful active benefit agents includes to simultaneously treat acne and pigmentation includes 4-hexyl resorcinol, N-acetyl glucosamine, gluconolactone, niacinamide, azelaic acid, and resveratrol.

The composition may be a cosmetic composition (which may or may not include additional active ingredients for the treatment of skin) that is applied to the skin to alter or minimize the appearance of a skin artifact based on the image data supplied by the detector arrangement 110. In one particular embodiment, the composition comprises one or more reflectance modifying agents (RMAs) (any component useful for altering reflectance of the skin). For example, suitable RMAs may include inks, dyes, pigments, bleaching agents, chemically altering agents and other substances that may be used to alter the reflectance of the skin. Some suitable RMAs may include a transparent RMA, such as a dye or a diluted pigment. Other suitable RMAs may include an opaque RMA having high refractive index particles. In particular, the high refractive index particles may comprise particles having a refractive index of 2.0 or greater. In one specific example, the RMA may comprise particles of titanium dioxide. Specifically, the titanium dioxide particles may be uniformly distributed and/or suspended in the cosmetic composition.

The device 100 according to this embodiment further comprises a power source 160 for providing power to control and operate the device 100. It is contemplated that the power source 160 may be located anywhere within the device 100 or external to the device 100. In one exemplary embodiment, the power source 160, which is shown in FIG. 1 as housed within the handle portion 104 of the device 100, is operably connected to the detector arrangement 110, the applicator arrangement 120 and/or the processing arrangement 130. Those skilled in the art will understand that various known suitable sources of power may be used. For example, the power source 160 may comprise a battery or a connection to an external source of power. In particular, the power source 160 may comprise a rechargeable battery device.

In use, the head portion 102 is placed over an area of skin that is to be treated. During use, the device 100 may be utilized to image a plurality of different areas of skin. For example, the head portion 102 may be moved across a surface of the skin allowing the device 100 to continuously image (at any desired frame rate) different areas of the skin to obtain image data and analyze the image data to selectively apply the composition to desired frexels on the skin. More particularly, the user may move the head portion 102 back and forth across the surface of the skin in multiple passes to allow the device 100 to review previously treated areas to detect skin artifacts which were missed or incompletely addressed and further apply the composition to artifacts on the skin.

The present application includes methods for selectively applying a composition to skin of a face of a user. In particular, the methods of the present application apply the composition to the skin in a manner such that the skin appears even toned, instead of blotchy or streaked, preferably, after any number of passes across the surface of the skin.

Figure 2:
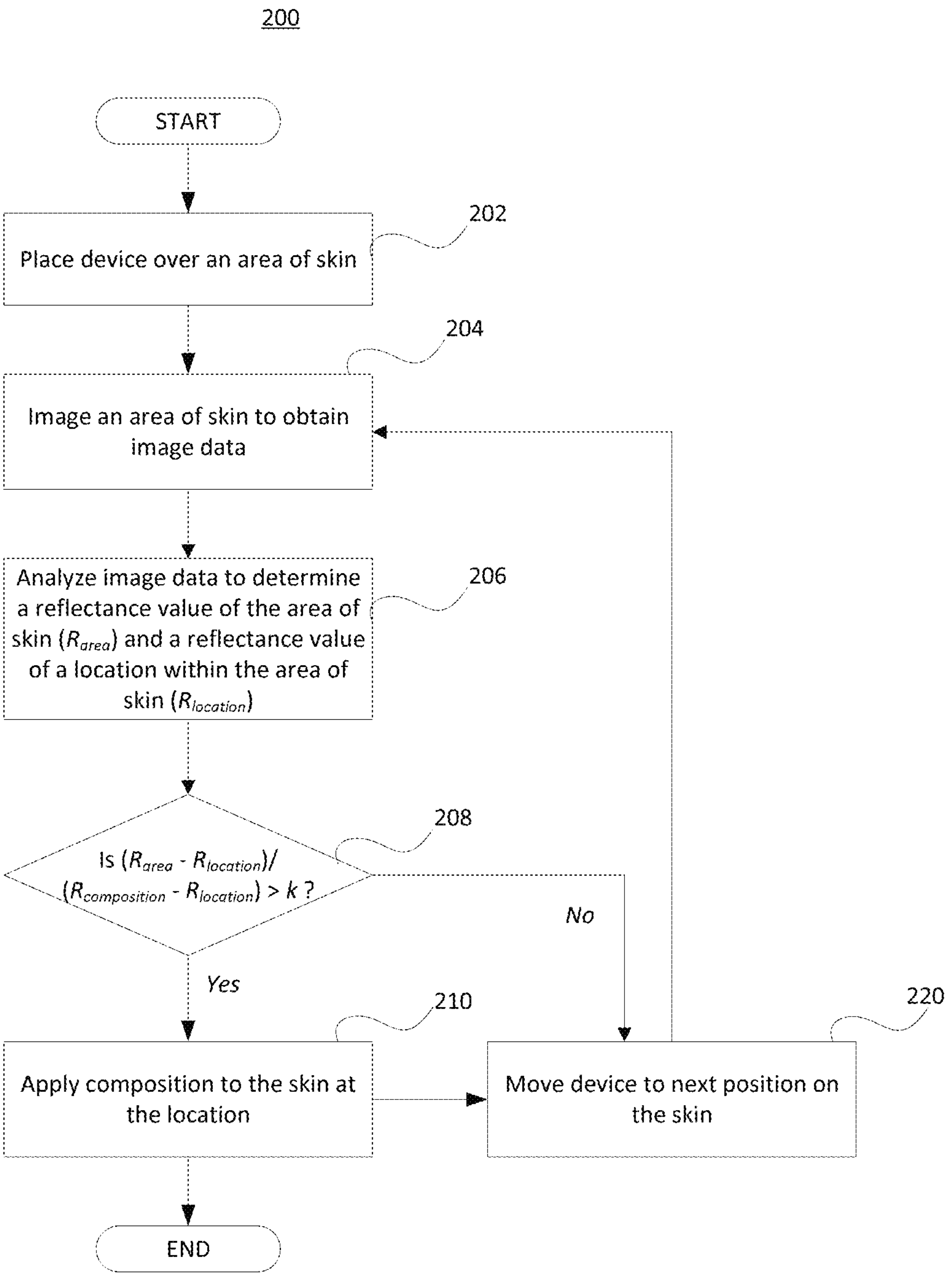
FIG. 2 shows an exemplary method for selectively applying a topical composition to the skin of a user, according to an exemplary embodiment of the present application.

An exemplary method 200 for selectively applying a composition to skin of a face of a user is shown in FIG. 2. The composition imparts an increase in reflectance (e.g., lightening in appearance) upon application to the skin. In step 202, the user may place a head portion 102 of the device 100 on the surface of skin. In step 204, the device 100, in particular, the detector arrangement 110, may sense and/or image an area of skin over which the device 100 is positioned to obtain image data. Specifically, light from the light source(s) 111 illuminate the area of skin and the sensor(s) 112 detect light from the area of skin to generate image data. The area of skin may be in any suitable shape, such as, for example, square, circular, rectangular, etc.

In step 206, the device 100, in particular, the processing arrangement 130, analyzes the image data to determine a reflectance value of the area of skin ($R_{area}$) imaged by the device 100 and a reflectance value of a location ($R_{location}$) within the area of skin imaged by the device 100. The location is a smaller area of the surface of the skin within the entirety of the area of skin imaged by the device. In particular, the location is an area of skin to which the applicator arrangement 120 is aimed (i.e., a frexel or frexels to which a drop emitted from the applicator arrangement 120 would be applied in the current alignment of the device relative to the skin).

The reflectance value of the area of skin may be obtained as an average reflectance value of the frexels within the area of skin. In some embodiments, the reflectance value of the location is determined, by the processing arrangement 130, as the reflectance value of a frexel located at a center of the location. In other embodiments, the reflectance value of the location is determined by the processing arrangement 130 as an average reflectance value of the frexel(s) to which the composition would be applied by the applicator arrangement 120. Specifically, the reflectance value of the location is determined by the processing arrangement 130 as a mean or median reflectance value of the frexel(s) to which the composition is aimed to be applied by the applicator arrangement 120. The term "average" as used herein refers to any suitable representation of a set of values, and may be a linear average, mean, median, maximum, minimum or weighted average of reflectance values for the plurality of frexels within an area or location. Preferably, the average is a mean or median value.

In step 208, the processing arrangement 130 compares $R_{area}$ to $R_{location}$ to determine whether to direct the applicator arrangement 120 to deposit a topical composition to the location. Specifically, the processing arrangement 130 determines whether $(R_{area}-R_{location})/(R_{composition}-R_{location})>k$, where $R_{composition}$ is a reflectance value of the composition to be applied to the skin. If so, the method 200 proceeds to step 210. Otherwise, the method proceeds to step 220. The predetermined constant k may be any suitable value selected from a range between 0 and 1 for identifying locations having skin artifacts that are within the middle spatial frequencies for application of the composition to modify appearance of the skin. In one embodiment, k is from about 0.01 to about 0.3, from about 0.03 to about 0.2, or from about 0.05 to 0.15. In one exemplary embodiment, k is 0.1.

In step 210, the processing arrangement 130 directs the applicator arrangement 120 to selectively deposit a topical composition to the location, as determined by the processing arrangement 130 described above with respect to step 208. In particular, the applicator arrangement 120 applies a fixed amount of the composition to the location.

In step 220, the user may move the device 100 to a new position on the surface of the skin and method 200 returns to step 204 and images, analyzes and selectively applies topical composition, as determined by the device 100, to a new area of skin in the same manner described above. This movement to a new position may be detected by the device 100 by any suitable means, such as, for example, an accelerometer or image analysis. It is noted that the method 200 may be interrupted and terminated by the user before any one of steps 202 through 220 by any suitable operation, such as, for example, removing the device 100 from the skin or switching off the device, in particular, the power source of the device.

In one particular embodiment of method 200, the predetermined constant k is 0. In this embodiment, the processing arrangement 130 compares $R_{area}$ to $R_{location}$ to determine whether reflectance at the location is darker (e.g., lower in value) than the reflectance of the area of skin encompassing said location. If the reflectance at the location is darker than the reflectance of the area of skin encompassing said location, then the processing arrangement 130 directs the applicator arrangement 120 to deposit a topical composition to the location, as described further below in step 210. If the reflectance at the location is equal to or brighter (e.g., higher in value) than the reflectance of the area of skin encompassing said location, then the processing arrangement 130 directs the applicator arrangement 120 to omit application of the topical composition to the location in the current iteration of the method 200 and proceed to step 220. For example, the processing arrangement 130 in step 208 compares $R_{area}$ to $R_{location}$ by determining whether $R_{area}-R_{location}>0$. If so, the method 200 proceeds to step 210. Otherwise, the method proceeds to step 220.

By using this zero-value threshold for k in step 208 to determine whether or not to proceed to step 210, the processing arrangement 130 of the device 100 is likely to proceed to step 210 and direct the applicator arrangement 120 to deposit the topical composition in about half of the iterations of method 200 regardless of the smoothness of the appearance of skin. This is particularly useful for application of a topical composition that lightens (e.g., increases reflectance) to areas of skin having darkened appearance, such as, for example, the undereye region, areas of hyperpigmentation, melasma, rosacea, birthmark, large scars, etc. More particularly, these areas of skin have darken skin features that are sufficiently large to be within low spatial frequencies of an overall image of a desired portion of skin, typically reflecting an anatomical portion of the body, e.g., face, leg, arm, etc. For example, these larger areas of skin within low spatial frequencies on the skin of a face of user may be larger than the area of skin imaged by the device 100, for example, these larger areas of skin may have an average diameter of at least 5 mm, at least 10 mm, or at least 20 mm.

Furthermore, comparison of $R_{area}$ to $R_{location}$ as provided in step 208 provides a way for the processing arrangement 130 to select those locations where application of the composition reduces appearance of skin artifacts while providing for visually even/smooth application of the composition. In particular, the processing arrangement 130 selects those locations where skin artifacts are present (e.g., those locations have a darker appearance—lower reflectance value) so that application of the composition imparts a desired aesthetic appearance of the skin (e.g., brightening appearance of dark skin artifacts), and those locations where appearance of the skin would be least negatively impacted by application of the composition (e.g., appearing blotchy or streaked) so that the composition is applied in a visually even/smooth manner throughout repeated iterations of method 200 as the user moves the device 100 back and forth across the surface of the skin, in particular, the skin of the face, in multiple passes. By using a predetermined constant k of 0, the device 100 is able to apply the composition at an approximately constant average rate over repeated iterations. The method 200 provides targeted application of the composition to the skin in an even/smooth manner which is in contrast to conventional air brush application of a cosmetic composition where application of a composition is placed on to the skin at a constant rate without any type of selection based on the appearance of the underlying skin and can therefore, impart undesired blotchiness to the appearance of skin and reduce the overall aesthetic appearance of the skin.

This zero-value threshold for k may also be for application of a topical composition to lighten a broader area on the skin as desired, such as, for example, imparting regions of increased lightening to desired areas of the face, e.g., imparting increased reflectance to certain areas of the face so as to visually enhance the contours of the face. For example, the device 100 may be set, by manual input or as automatically determined by the processing arrangement 130, to a first mode where k is set to 0 while the device is placed over a region where additional lightening is desired. When the device 100 is moved to a different region of the face where additional lightening is not desired, the processing arrangement 130 may switch, by manual input or as automatically determined by the processing arrangement 130, to a second mode where the processing arrangement 130 determines whether $(R_{area}-R_{location})/(R_{composition}-R_{location})>k$, where k is greater than 0, and $R_{composition}$ is a reflectance value of the composition to be applied to the skin.

Although exemplary method 200 discussed above relates to application of a composition having a higher reflectance than an average reflectance of the skin of the user so as to lighten appearance of darken areas of skin, it is contemplated that the device 100 of the present application may also be used to selectively apply a composition having a lower reflectance (i.e., darker) than an average reflectance of the skin and to darken skin artifacts having lighter skin, such as, for example, vitiligo, tan lines, etc. The composition may, for example, be a bronzer or a tanning composition. For selective application of a composition to darken the appearance of skin while improving appearance of smoothness of the skin, the processing arrangement 130 may select those frexels for application of the composition in a similar manner as discussed above with respect to methods 200. In some embodiments, step 208 may be modified to compare $R_{area}$ to $R_{location}$ to select those locations where application of the composition reduces appearance of skin artifacts while providing for visually even/smooth application of the composition by determining, for example, whether $(R_{location}-R_{area})/(R_{location}-R_{composition})>k$.

Figure 3A:
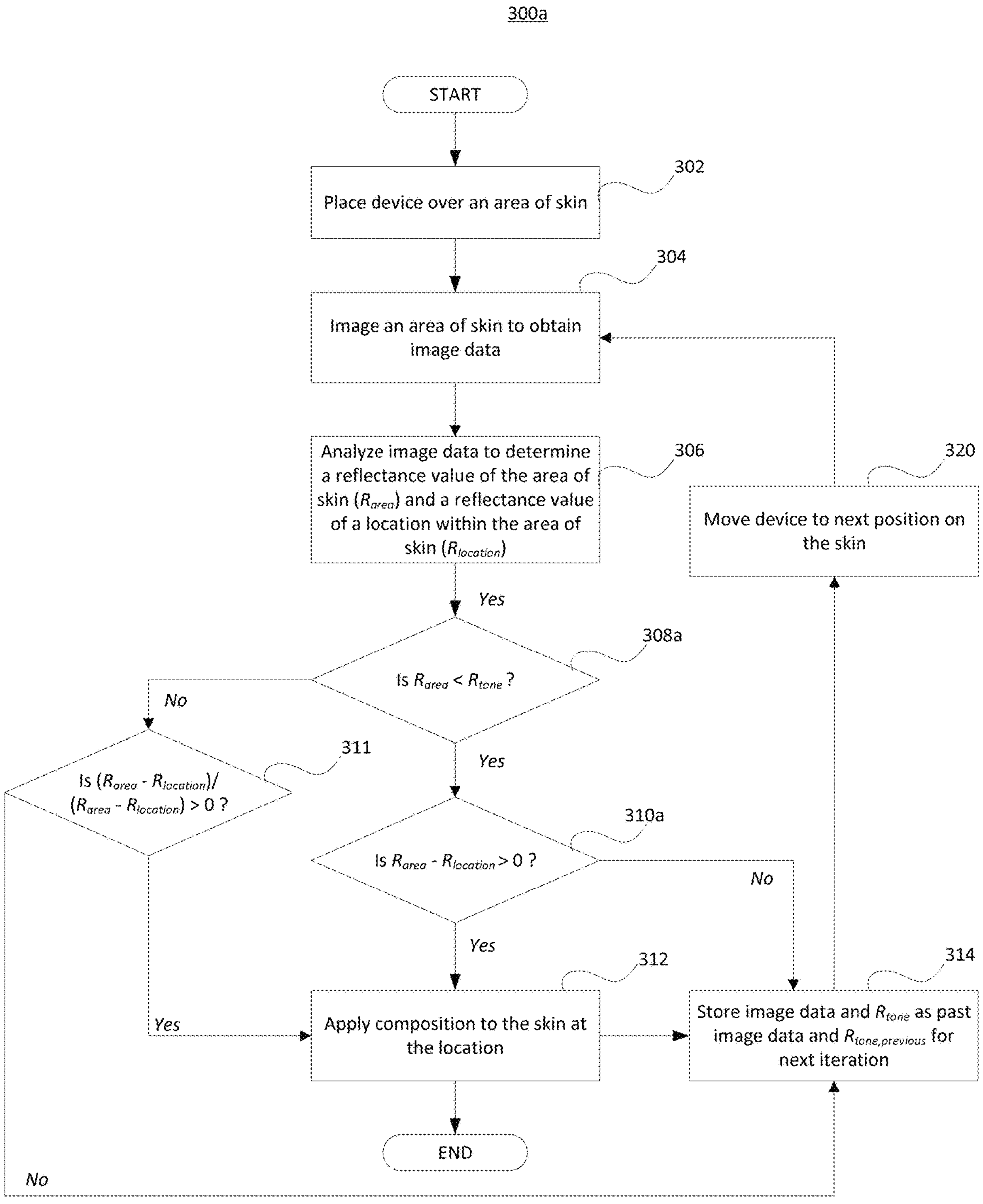
FIG. 3*a* shows another exemplary method for selectively applying a topical composition to the skin of a user, according to an exemplary embodiment of the present application.

In a further embodiment, FIG. 3*a* shows another exemplary method 300*a*. Method 300*a* allows the user to pass the device 100 repeatedly across a portion of the surface of the skin of the face and selectively apply the composition for any number of passes, without imparting an undesired blotchy or streaked appearance to the skin after each iteration of the method 300*a*. Therefore, method 300*a* allows the user to pass the device 100 partially across the surface of the skin of the face and selectively apply the composition for any number of passes, without imparting an undesired blotchy or streaked appearance to the skin. The method 300*a* includes some similar steps as method 200 described above. Notably, the method 300*a* includes a further step for identifying those locations that are darker (e.g., having a lower reflectance value) than reflectance of a selected tone, as explained further below. Therefore, the method 300*a* analyzes image data obtained from the area of skin imaged in step 304 as well as data for or relating to a selected tone e in determining whether a modification to an aesthetic appearance of skin is desired while maintaining an even/smooth appearance of the skin throughout each iteration of method 300*a*. Although exemplary method 300*a* is discussed below with reference to application of a composition having a higher reflectance than an average reflectance of the skin of the user so as to lighten appearance of darken areas of skin, similar to method 200 it is contemplated that a similar method to method 300*a* may also be used to selectively apply a composition having a lower reflectance (i.e., darker) than an average reflectance of the skin to skin artifacts having lighter skin (e.g., vitiligo, tan lines, etc.), which is discussed further below. The composition may, for example, be a bronzer or a tanning composition.

Steps 302 to 306 are the same as steps 202 to 206 discussed above. In step 308*a*, the processing arrangement 130 compares $R_{area}$ to a reflectance value of a selected tone ($R_{tone}$).Skin at locations that are darker (e.g., having a lower reflectance value) than the selected tone are identified for application of the composition in step 312. The processing arrangement 130 bypasses step 310*a* for skin at locations that are at or above the reflectance value of the selected tone and determines whether or not to apply the composition to the skin via step 311. More particularly, the processing arrangement 130 in step 308*a* compares $R_{area}$ to the reflectance value of the selected tone ($R_{tone}$) to an determine whether the reflectance at the area of skin imaged in step 304 is darker (e.g., lower in value) than the reflectance of the selected tone. If the reflectance of the area of skin is darker than the reflectance of the selected tone, then the processing arrangement 130 directs the applicator arrangement 120 to step 310*a*. If the reflectance of the area of skin is equal to or brighter (e.g., higher in value) than the reflectance of the selected tone, then the processing arrangement 130 proceeds to step 310*a*. In one exemplary embodiment, the processing arrangement 130 in step 308*a* compares $R_{area}$ to $R_{tone}$ by determining whether $R_{area}-R_{tone}>0$. If so, the method 300*a* proceeds to step 310*a*. Therefore, the method 300*a* sets $R_{tone}$ as a goal reflectance value to which the device 100 applies the composition. Otherwise, the method proceeds to step 311.

The reflectance value of the selected tone ($R_{tone}$) may be a predetermined constant value tone, for the duration of a use session or may be dynamically determined for each iteration of method 300. In one embodiment, $R_{tone}$ may be a predetermined value stored within the memory storage device 170. In some embodiments, a constant $R_{tone}$ for a use session may be determined based on data collected from prior sessions of use of the device 100. In another embodiment, the $R_{tone}$ may be determined by user input prior to initiating a use session. For example, the device 100 may include a user interface for receiving input for a selection of a desired $R_{tone}$ from the user. In another example, the device 100 may be manually triggered into a separate mode for inputting a desired $R_{tone}$. In this separate mode, the user puts the device 100 over an area of skin having a desired reflectance. The device 100, in particular, the detector arrangement 110, senses and/or images the area of skin selected by the user to obtain image data. The processing arrangement 130, analyzes the image data to determine a reflectance value for the selected area of skin as $R_{tone}$. The $R_{tone}$ may be obtained as an average reflectance value of the frexels within the area of skin selected by the user, wherein the term "average" is as defined above.

In other embodiments, $R_{tone}$ is dynamically determined for each iteration of method 300. In one embodiment, the $R_{tone}$ is determined based on reflectance values of a region of skin near, adjacent and/or surrounding, at least in part, the area of skin imaged by the detector arrangement 110. The region of skin may be in any suitable shape, such as, for example, square, circular, rectangular, etc. The region of skin may be at least the same size or larger than the area of skin imaged by the detector arrangement 110. The region of skin may overlap, at least in part, with the area of skin imaged by the detector arrangement. Alternatively, the region of skin may be adjacent to, without any overlap, the area of skin imaged by the detector arrangement 110. In some embodiments, the region of skin may be concentric with the area of skin imaged by the detector arrangement 110. In other embodiments, the region of skin may be non-concentric with the area of skin imaged by the detector arrangement 110. In one particular embodiment, the region of skin for determining $R_{tone}$ is larger than and overlaps with the area of skin imaged by the detector arrangement 110, and is preferably non-concentric with the area of skin. In another embodiment, the region of skin for determining $R_{tone}$ is larger than and adjacent to, without any overlap, the area of skin imaged by the detector arrangement 110, and is preferably non-concentric with the area of skin.

The $R_{tone}$ may be dynamically determined for each iteration of method 300*a* based on past image data. The past image data may be any image data obtained by the detector arrangement 110 in prior use of the device 100, including prior use sessions and/or prior iterations of method 300*a* within the same use session. Prior image data corresponding to frexels within the region of skin as discussed above may be used to determine the $R_{tone}$. For example, $R_{tone}$ may be obtained as an average reflectance value of the frexels within the region of skin based on past image data of those frexels. In one embodiment, the device 100 is positionally aware of placement of the device 100 relative to a face of the user and map image data generated by the device 100 for each iteration of the method 300*a* to an anatomical mapping of the face of the user. For example, the device 100 may be positionally aware of the placement of the device 100 relative to the face of the user and select those regions near the cheek bone of the face for increased lightening. In one example, the device 100 may be positionally aware of placement of the device 100 relative to various markers corresponding to key positions on a face of the user. In another example, the device 100 may be positionally aware of placement of the device 100 relative to various facial regions (e.g., eyelids, eyeballs, eyelashes, nose, cheeks, lips, etc.) on a face of the user. In a further example, the device 100 may generate a map and/or a composite image of a face of a user as the user moves the head portion 102 back and forth across the surface of the skin in multiple passes during use, and the device 100 may identify placement of the device 100 relative to the map and/or the composite image. The device 100 selects past image data corresponding to those frexels within a desired region of skin overlapping with or adjacent to the area of skin currently imaged by the device 100 to determine an average reflectance value of those frexels as the $R_{tone}$.

In one particular exemplary embodiment, the region of skin may be the skin for the entirety of the face. The $R_{tone}$ may be dynamically determined for each iteration of method 300*a* based on a running average of reflectance values ($R_{average}$) for all areas of skin imaged by the device 100 in previous iterations of method 300*a* within a use session. Specifically, the $R_{tone}$ is a mean or median reflectance value of all past image data corresponding to all frexels imaged d by device 100 within the same use session. In some embodiments, use of $R_{average}$ as the $R_{tone}$ may cause the device 100 to apply the composition in a manner such that it over aggressively modifies the appearance of the skin. Therefore, $R_{tone}$ may be $R_{average}$ modified by a constant multiplier n, where n can be any value between 0 and 1. In particular, n may be selected based on the user's skin tone and/or the level of uniformity in appearance of the skin desired by the user from application of the composition by the device 100 through repeated iterations of method 300*a*. In one embodiment, n is determined based on past image data of the user. A value for n may be selected be a predetermined value stored within the memory storage device 170. A higher value for n will allow the device 100 to more aggressively modify (e.g., apply the composition to those locations having a less difference from $R_{tone}$) an uneven appearance of the skin. In one particular embodiment, n may be 0.67 or 1/1.5.

In another embodiment, the $R_{tone}$ is determined using past image data corresponding to image data for an area of skin previously imaged by the detector arrangement 110 within the same use session, as the head portion 102 was moved by the user back and forth across the surface of the skin in previous passes within the same use session. In particular, the $R_{tone}$ is determined using past image data corresponding to image data for at least one area of skin adjacent to the area of skin imaged in step 304. In another example, the past image data corresponds to image data for an area of skin that was imaged immediately prior to the area of skin imaged in step 304. In further embodiments, the past image data includes image data of a plurality of areas of skin that were imaged immediately prior to the area of skin imaged in step 304. Specifically, the past image data includes data corresponding to a predetermined number of images of areas of skin that were imaged immediately prior to the area of skin imaged in step 304. The predetermined number of images may be from 1 to 25, or from 3 to 10. In one particular embodiment, the predetermined number of images is 4 or 5. In another example, the past image data for determining $R_{tone}$ may include data corresponding to images of areas of skin that were imaged within a predetermined amount of time prior to the area of skin imaged in step 304.

In a further exemplary embodiment, the $R_{tone}$ is determined using past image data corresponding to certain areas of skin that were imaged immediately prior to the area of skin imaged in step 304. In particular, the $R_{tone}$ may be determined using past image data corresponding to (1) images of areas of skin having each having a reflectance of greater than a predetermined threshold within a first predetermined number ($m_{light}$) of images prior to the area of skin imaged in step 304, and (2) images of areas of skin having each having a reflectance of less than the predetermined threshold within a second predetermined number ($m_{dark}$) of images prior to the area of skin imaged in step 304, where $m_{light}$ is greater than $m_{dark}$. For application of a composition that darkens the appearance of skin, $m_{light}$ may be less than $m_{dark}$.

In another embodiment, the $R_{tone}$ may be determined using past image data corresponding to (1) images of areas of skin having each having a reflectance of greater than a predetermined threshold within a first predetermined amount of time ($t_{light}$) prior to the area of skin imaged in step 304, and (2) images of areas of skin having each having a reflectance of less than the predetermined threshold within a second predetermined amount of time ($t_{dark}$) prior to the area of skin imaged in step 304, where $t_{light}$ is longer than $t_{dark}$. In a further embodiment, for application of a composition that darkens the appearance of skin, $t_{light}$ may be longer than $t_{dark}$.

These exemplary embodiments are particularly useful when a user repeatedly passes the device 100 between a darker area of skin, such as, for example, the undereye region, and a lighter area of skin, such as, for example, areas of skin near the cheekbone on a face of the user. For example, the user may repeatedly pass the device between the skin of the undereye region and the skin of the cheeks of the face of the user in an up and down brushing motion. As the device 100 is moved towards a lighter region of skin, the $R_{tone}$ in these exemplary embodiments would be adjusted to have a higher reflectance value (i.e., lighter). In contrast, as the device 100 is moved towards a darker region of skin (such as the undereye region, or regions of skin having a skin artifact, e.g., areas of hyperpigmentation, melasma, rosacea, birthmark, large scars, etc.), the $R_{tone}$ in these exemplary embodiments would not be as rapidly adjusted to have a lower reflectance value (i.e., darker) and thereby weighting the selective application of the composition by the device 100 towards those regions of skin having lower reflectance values and thereby reduce appearance of darken regions of skin. Such dynamic adjustments to $R_{tone}$ further improves the smooth appearance of skin after each iteration of method 300*a* and reduces undesired blotchy or streaked appearance as the composition is applied to the skin through each iteration of method 300*a*.

In one particular embodiment, in the first iteration of method 300*a*, $R_{tone}$ may be assigned a predetermined value. For example, the predetermined value may correspond to a level of skin brightening generally desired by the user. The predetermined value may be a default value assigned by the device 100 or a setting determined on the device 100 and selected by the user. In subsequent iterations of method 300*a*, $R_{tone}$ is determined based the past image data, as well as a reflectance value of a previously selected tone ($R_{tone,\ previous}$) for analyzing the past image data. In one exemplary embodiment, $R_{tone}$ is determined as a function of $R_{tone,\ previous}$, a reflectance value of the area of skin corresponding to the past image data ($R_{area,\ previous}$) and a reflectance value of a previously analyzed location within the area of skin corresponding to the past image data ($R_{location,\ previous}$). Specifically, $R_{tone}$ may be determined as a function of $R_{tone,\ previous}$, $R_{area,\ previous}$, and the reflectance value the lighter of the previous area of skin imaged by the device 100 or the previously analyzed location within the previously imaged area of skin (e.g., a maximum value from the set of $R_{area,\ previous}$ and $R_{location\ previous}$). The $R_{tone,\ previous}$ may be a predominate contributor to the determination of $R_{tone}$, with $R_{area,\ previous}$ and the maximum of $R_{area,\ previous}$ and $R_{location\ previous}$ modifying $R_{tone,\ previous}$ to obtain an adjusted value for $R_{tone}$. This adjustment to the reflectance value of the selected tone based on reflectance of the previously imaged area of skin provides gradual adjustments to the selected tone and thereby allowing for the composition to be applied to the skin in a gradual and visually even/smooth manner across iterations of method 300*a*. For example, $R_{tone}$ may be determined as follows:

$$R_{tone}=xR_{tone,\ previous}+yR_{area,\ previous}+y\max(R_{area,\ previous},R_{location,\ previous})$$

wherein x+2y=1. x may be any suitable number between 0 and 1. x may be adjusted based on a rate of changed in tone desired between iterations of the method 300*a*. As discussed above, the $R_{tone,\ previous}$ may be a predominate contributor to the determination of $R_{tone}$ and therefore, x may be from about 0.8 to 0.998. In particular, x may be from about 0.9 to 0.99. In one preferred embodiment, x is 0.98.

In an alternative embodiment, the $R_{tone}$ be dynamically determined for each iteration of method 300 based on image data collected by the detector arrangement. In this embodiment, the detector arrangement 110 is configured to image both an area of skin over which the device 100 is placed and a region of skin near, adjacent and/or surrounding, at least in part, the area of skin. For example, the detector arrangement 110 may include a plurality of sensors 112 comprising a first sensor configured to detect reflectance of light from an area of skin and a second sensor configured to detect reflectance of light from a region of skin near, adjacent and/or surrounding, at least in part, the area of skin. In this embodiment, the $R_{tone}$is dynamically determined for each iteration of the method 300*a* based on image data for the region of imaged skin by the detector arrangement 110.

In step 310, the processing arrangement 130 compares $R_{area}$ to $R_{location}$ to determine whether reflectance at the location is darker (e.g., lower in value) than the reflectance of the area of skin encompassing said location. If the reflectance at the location is darker than the reflectance of the area of skin encompassing said location, then the processing arrangement 130 directs the applicator arrangement 120 to deposit a topical composition to the location in step 312. If the reflectance at the location is equal to or brighter (e.g., higher in value) than the reflectance of the area of skin encompassing said location, then the method 300*a* omits application of the topical composition to the location in the current iteration and proceed to step 314. Step 312 corresponds to step 210 as described above.

Although FIG. 3*a* illustrates the comparisons of steps 308*a* and 310*a* in a particular order, it is noted that steps 308*a* and 310*a* may be performed in the order as shown in FIG. 3*a*, may be performed in a reverse order as compared that shown in FIG. 3*a*, i.e., step 310*a* before step 308*a*, or may be performed simultaneously together. For example, the processing arrangement 130 may compare $R_{area}$ to $R_{tone}$ and $R_{location}$, and only proceed to step 312 when both $R_{area}$ is less than $R_{tone}$ and $R_{location}$ is less than $R_{area}$ (e.g., $R_{area}>R_{location}$ or $R_{area}-R_{location}>0$).

Step 311 is substantially similar to step 208 described above. Specifically, the processing arrangement 130 determines whether $(R_{area}-R_{location})/(R_{composition}-R_{location})>k$, where $R_{composition}$ is a reflectance value of the composition to be applied to the skin. If so, the method 300*a* proceeds to step 312. Otherwise, the method proceeds to step 314. The predetermined constant k may be any suitable value selected from a range greater than 0 and less than or equal to 1 for identifying locations having skin artifacts that are within the middle spatial frequencies for application of the composition to modify appearance of the skin.

Following application of the composition in step 312, the method 300*a* proceeds to step 314. In step 314, the processing arrangement 130 updates the past image data to include the image data of the current iteration of method 300*a*. More particularly, the device 100 stores, in a memory storage device 170, the image data, which may include $R_{area}$ and $R_{location}$, and $R_{tone}$ of the current iteration of method 300*a* as past image data and $R_{tone, previous}$ for the next iteration of the method 300*a*. In one embodiment, the processing arrangement 130 stores the image data from step 304, $R_{area}$, $R_{location}$ and $R_{tone}$ in the memory storage device 170 so that it is subsequently retrievable by the processing arrangement 130 as past image data, $R_{area, previous}$, $R_{location, previous}$ and $R_{tone, previous}$ in a subsequent iteration of the method 300*a*.

Step 314 is the same as step 210 described above. Following step 314, the method 300*a* proceeds to step 320, which is the same as step 220 described above. Similar to method 200, the method 300*a* may be interrupted and terminated by the user before any one of steps 302 through 320 by any suitable operation, such as, for example, removing the device 100 from the skin or switching off the device, in particular, the power source of the device.

Although exemplary method 300*a* is discussed below with reference to application of a composition having a higher reflectance than an average reflectance of the skin of the user so as to lighten appearance of darken areas of skin, similar to method 200 it is contemplated that a similar method to method 300*a* may also be used to selectively apply a composition having a lower reflectance (i.e., darker) than an average reflectance of the skin, such as, for example, a bronzer or a tanning composition, which is discussed further below.

For selective application of a composition to darken the appearance of skin while improving appearance of smoothness of the skin, the processing arrangement 130 may select those frexels for application of the composition in a similar manner as discussed above with respect to methods 300*a*, except steps 308*a* and 310*a* are modified to compare $R_{area}$ to $R_{tone}$ and $R_{location}$ in a reversed comparison. Specifically, when the device 100 is used to apply a composition having a lower reflectance than average reflectance of the skin, step 308*a* is modified to determine whether $R_{tone}<R_{area}$ and step 310*a* is modified to determine whether $R_{location}-R_{area}>0$. In addition, step 311 may also be modified to determine whether $(R_{location}-R_{area})/(R_{location}-R_{composition})>k$.

Figure 3B:
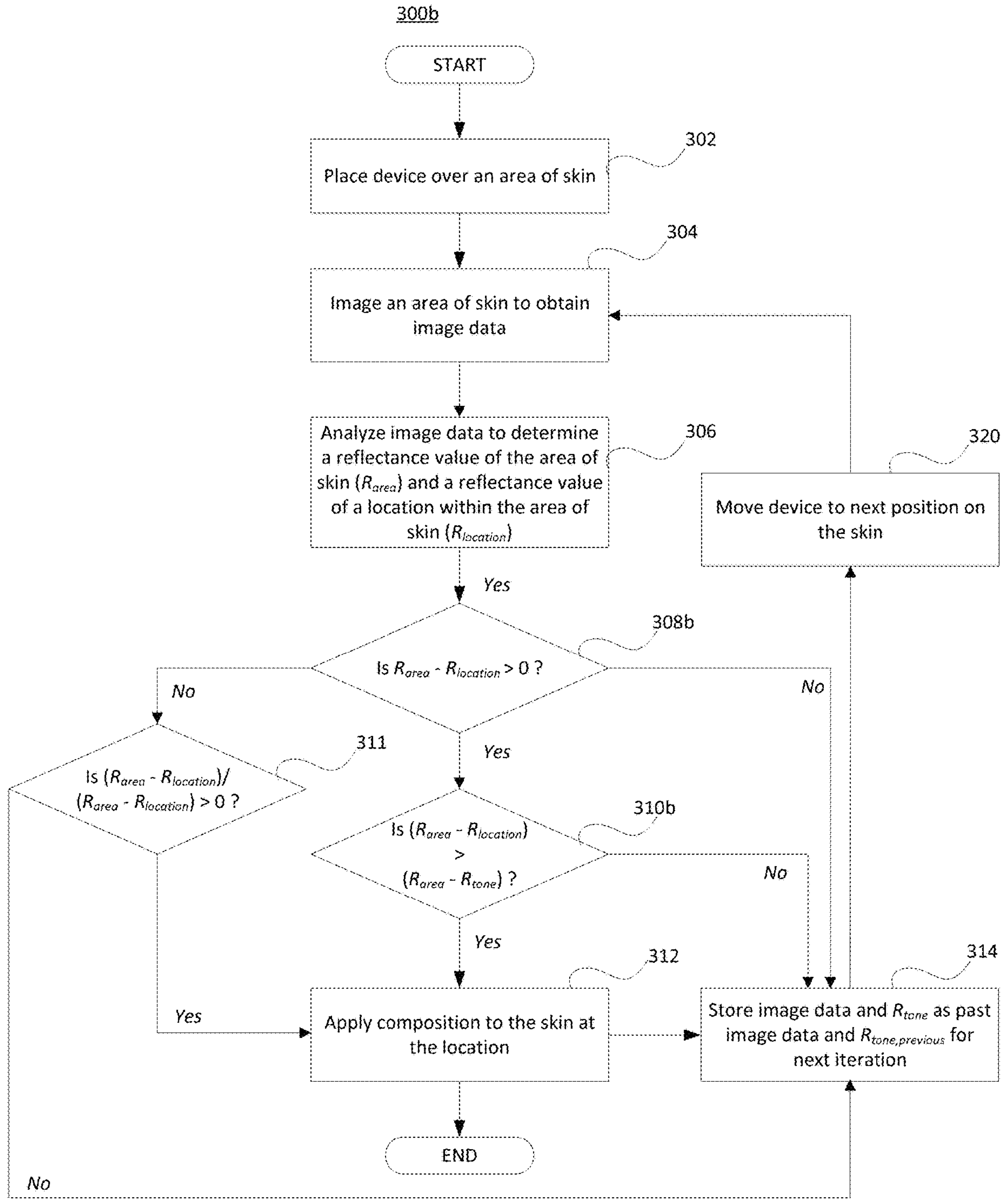
FIG. 3*b* shows an alternative exemplary method for selectively applying a topical composition to the skin of a user, according to an exemplary embodiment of the present application.

In another embodiment, FIG. 3*b* shows an exemplary method 300*b*. The method 300*b* is similar to method 300*a* described above. Similar to method 300*a*, method 300*b* allows the user to pass the device 100 repeatedly across a portion of the surface of the skin of the face and selectively apply the composition for any number of passes, without imparting an undesired blotchy or streaked appearance to the skin after each iteration of the method 300*b*. Therefore, method 300*b* allows the user to pass the device 100 partially across the surface of the skin of the face and selectively apply the composition for any number of passes, without imparting an undesired blotchy appearance to the skin. The method 300*b* shown in FIG. 3*b* also includes a step that limits application of the composition to those locations darker than a reflectance of a selected tone as determined by past imaged data. Method 300*b* is substantially the same as method 300*a* except in steps 308*b* and 310*b*, as shown in FIG. 3*b*.

The combination of steps 308*b* and 310*b* provides the same type of selection of locations for application of cosmetic composition as steps 308*a* and 310*a* described above for method 300*a*. Step 308*b* is similar to steps 208 and 310*a* described above. In particular, the processing arrangement 130 compares $R_{area}$ to $R_{location}$ to determine whether reflectance at the location is darker (e.g., lower in value) than the reflectance of the area of skin encompassing said location. If the reflectance at the location is darker than the reflectance of the area of skin encompassing said location, then the method 300*b* proceeds to step 310*b*. If the reflectance at the location is equal to or brighter (e.g., higher in value) than the reflectance of the area of skin encompassing said location, then method 300*b* omits application of the topical composition to the location in the current iteration and proceed to step 320.

In step 310*b*, the processing arrangement 130 compares $R_{area}$ and/or $R_{location}$ to the reflectance value of a selected tone ($R_{tone}$), which is determined as described above with respect to method 300*a*. In one exemplary embodiment, the processing arrangement in step 310*b* determines whether $R_{area}-R_{location}>R_{area}-R_{tone}$. If so, the method 300*b* proceeds to step 312. Otherwise, the method proceeds to step 311. Similar to FIG. 3*a*, although FIG. 3*b* illustrates the comparisons of steps 308*b* and 310*b* in a particular order, it is noted that steps 308*b* and 310*b* may be performed in the order as shown in FIG. 3*b*, may be performed in a reverse order as compared that shown in FIG. 3*b*, i.e., step 310*b* before step 308*b*, or may be performed simultaneously together.

Similar to method 300*a*, it is contemplated that a method similar to method 300*b* may also be used to selectively apply a composition having a lower reflectance (i.e., darker) than an average reflectance of the skin, such as, for example, a bronzer or a tanning composition. For selective application of a composition to darken the appearance of skin while improving appearance of smoothness of the skin, the processing arrangement 130 may select those frexels for application of the composition in a similar manner as discussed above with respect to methods 300*b*, except steps 308*b* and 310*b* are modified to compare $R_{area}$ to $R_{tone}$ and $R_{location}$ in a reversed comparison. Specifically, when the device 100 is used to apply a composition having a lower reflectance than average reflectance of the skin, step 308*b* is modified to determine whether $R_{location}-R_{area}>0$ and step 310*b* is modified to determine whether $R_{location}-R_{area}>R_{area}-R_{tone}$. In addition, step 311 may also be modified to determine whether $(R_{location}-R_{area})/(R_{location}-R_{composition})>k$.

Figure 4:
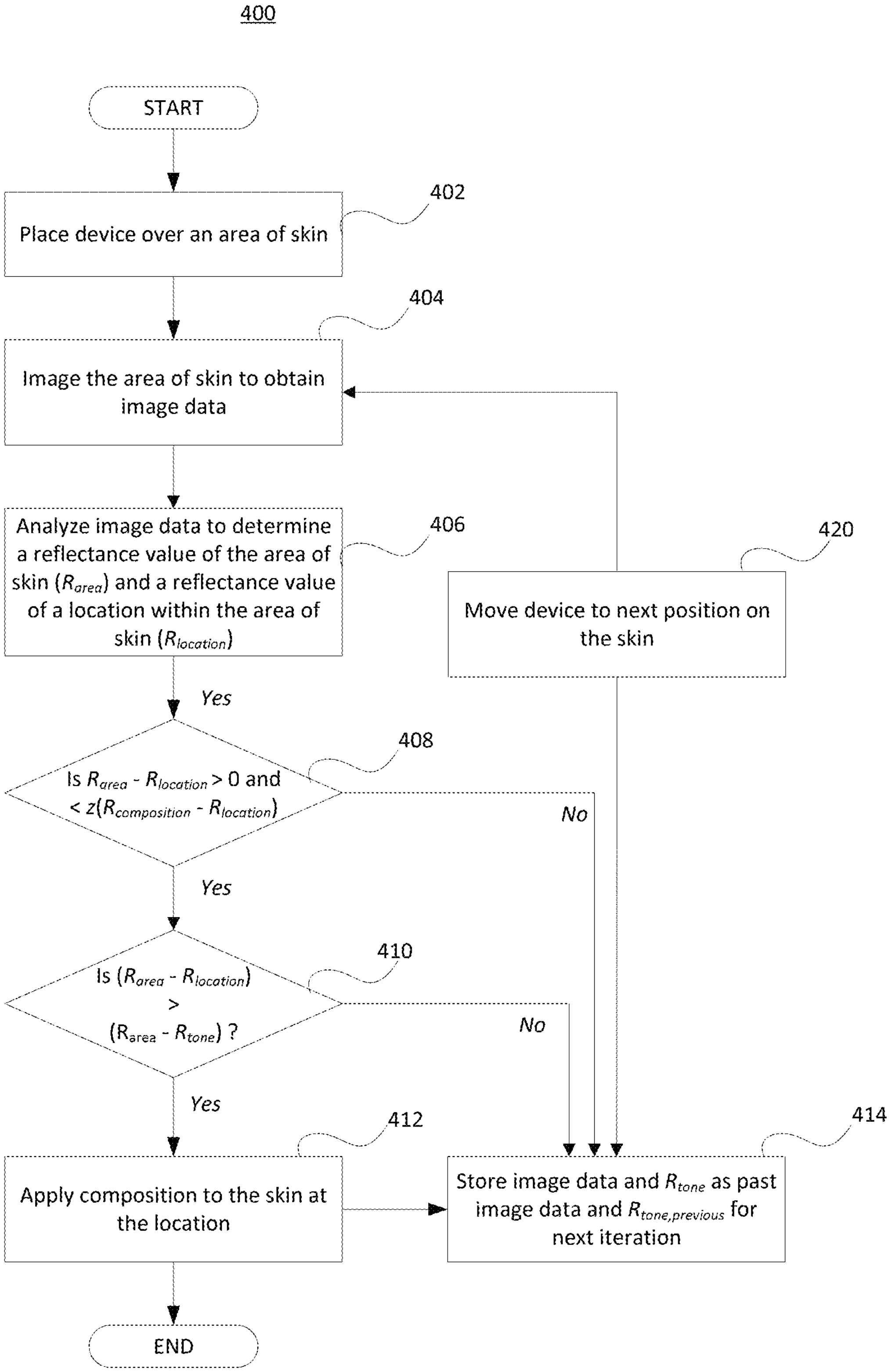
FIG. 4 shows a further exemplary method for selectively applying a topical composition to the skin of a user, according to an exemplary embodiment of the present application.

FIG. 4 provides a further exemplary method 400 for selectively applying a composition to skin of a user. The method 400 is similar to method 300*b* described above, except as otherwise indicted below. Similar to method 300*a* and 300*b*, method 400 allows the user to pass the device 100 repeatedly across a portion of the surface of the skin of the face and selectively apply the composition for any number of passes, without imparting an undesired blotchy or streaked appearance to the skin after each iteration of the method 400. Therefore, method 400 allows the user to pass the device 100 partially across the surface of the skin of the face and selectively apply the composition for any number of passes, without imparting an undesired blotchy appearance to the skin. Notably, the method 400 includes a further step limiting application of the composition by the applicator arrangement 120 to those locations corresponding to skin artifacts within middle spatial frequencies of a surface of skin of the user, in particular the face of the user. Therefore, the method 400 analyzes image data obtained from the area of skin imaged in step 404 as well as past image data in determining whether and how much of a modification to an aesthetic appearance of skin is desired while maintaining an even/smooth appearance of the skin that targets skin artifacts within middle spatial frequencies of a surface of skin throughout repeat iterations of method 400.

Steps 402 to 406 are the same as steps 302 to 306 discussed above. In step 408, the processing arrangement 130 analyzes the image data to determine whether a location within the area of skin image by the device 100, preferably a location to which the applicator arrangement 120 is aimed, corresponds to skin artifacts within middle spatial frequencies of a surface of skin of the user. In particular, the processing arrangement 130 compares the reflectance value of the area of skin to a reflectance value of a selected tone. The processing arrangement 130 in step 408 also compares a difference of the reflectance value of the area of skin and the reflectance value of the location to a predetermined percentage of a difference of a reflectance value of the composition and the reflectance value of the location. The predetermined percentage may be selected for filtering and/or identifying those locations having skin artifacts that are within the middle spatial frequencies of the surface of the skin. In one exemplary embodiment, the processing arrangement 130 in step 408 determines whether $R_{area}-R_{location}$ is between 0 and $z(R_{composition}-R_{location})$, where $R_{area}$ and $R_{location}$ are as defined above, $R_{composition}$ is a reflectance value of the composition to be applied to the skin, and z is a constant selected from a range greater than 0 and less than or equal to 1 for identifying locations having skin artifacts that are within the middle spatial frequencies for application of the composition to modify appearance of the skin. The predetermined constant z may be any suitable value for identifying those locations having skin artifacts that fall within middle spatial frequencies. In one embodiment, z is from about 0.01 to about 0.3, from about 0.03 to about 0.2, or from about 0.05 to 0.15. Preferably, z is 0.1. If the processing arrangement 130 determines that $R_{area}-R_{location}$ is between 0 and $z(R_{composition}-R_{location})$, then the method 400 proceeds to step 410, which is the same type of comparison as described in step 310*b* above. Steps 412, 414 and 420 of method 400 are the same as steps 310*b*, 312, 314 and 320 described above. Similar to FIGS. 3*a* and 3*b*, although FIG. 4 illustrates the comparisons of steps 408 and 410 in a particular order, it is noted that steps 408 and 410 may be performed in the order as shown in FIG. 4, may be performed in a reverse order as compared that shown in FIG. 4, i.e., step 410 before step 408, or may be performed simultaneously together.

Although exemplary method 400 discussed above relates to application of a composition having a higher reflectance than an average reflectance of the skin of the user so as to lighten appearance of darken areas of skin, similar to methods 200, 300*a* and 300*b*, it is contemplated that the device 100 of the present application may also be used to selectively apply a composition having a lower reflectance (i.e., darker) than an average reflectance of the skin to skin artifacts having lighter skin, such as, for example, vitiligo, tan lines, etc. The composition may, for example, be a bronzer or a tanning composition. For selective application of a composition to darken the appearance of skin while improving appearance of smoothness of the skin, the processing arrangement 130 may select those frexels for application of the composition in a similar manner as discussed above with respect to methods 400, except steps 408 and 410 are modified to compare $R_{area}$ to $R_{tone}$ and $R_{location}$ in a reversed comparison. Specifically, when the device 100 is used to apply a composition having a lower reflectance than average reflectance of the skin, step 408 is modified to determine whether $R_{location}-R_{area}>0$ and $<z(R_{location}-R_{composition})$ and step 310*a* is modified to determine whether $R_{location}-R_{area}>R_{tone}-R_{area}$.

EXAMPLE

Example 1

Figure 5:
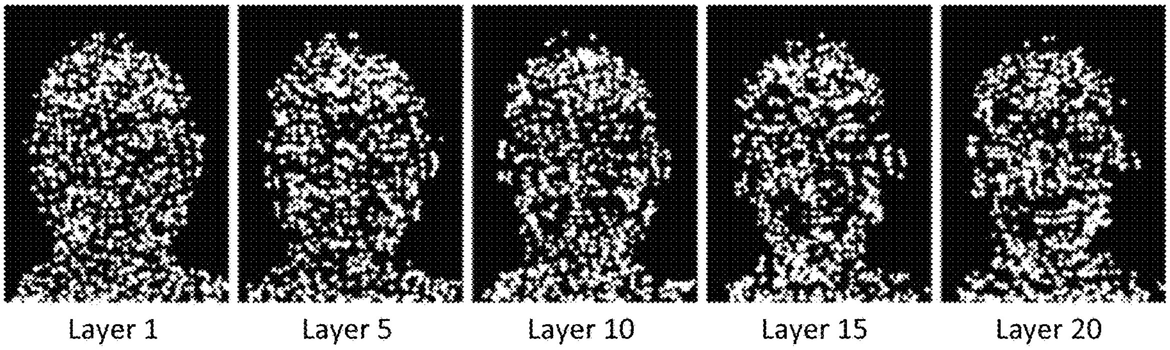
FIG. 5 shows an exemplary series of distributions of a topical composition simulated to be applied to skin of a face of a user according to the exemplary method of FIG. 2.
Figure 6:
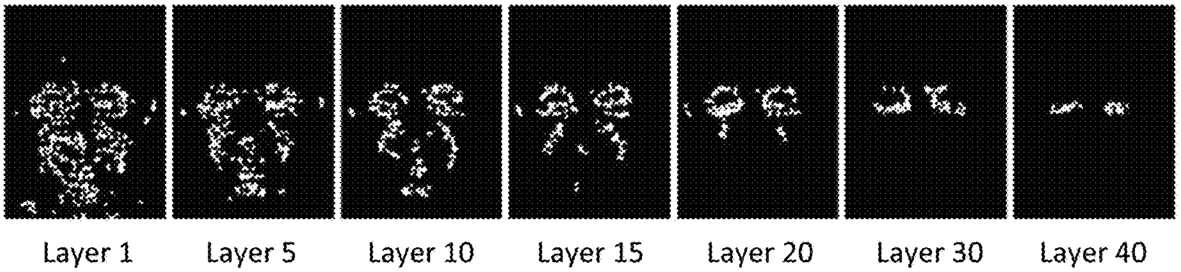
FIG. 6 shows another exemplary series of distributions of a topical composition simulated to be applied to skin of a face of a user according to the exemplary method of FIG. 3*b*.
Figure 7:
FIG. 7 shows a computer simulated image for an accumulated distribution of the topical composition as applied in FIG. 5.

Images for computer-simulated application of a cosmetic composition repeating through numerous passes across the same simulated surface of skin are provided in FIGS. 5 and 6. FIG. 5 shows a series of computer-simulated images showing distribution of the cosmetic composition applied by iterating the method 200 of FIG. 2. Each image in FIG. 5 is numerically numbered for the number of layers of the composition that is simulated to be applied. Each layer corresponds to one simulated pass of the device 100 across the entirety of the face of a user. As can be seen in FIG. 5, the cosmetic composition is applied in approximately similar amounts across the different layers. FIG. 7 shows a computer-simulated image for an accumulated distribution of the cosmetic composition as applied in FIG. 5. The image of FIG. 7 shows that the method 200 applies the cosmetic composition in a manner that builds up across the face but particularly targets those areas having skin artifacts to thereby improve the appearance of skin (e.g., improving appearance of smoothness of the skin).

Figure 8:
FIG. 8 shows a computer simulated image for an accumulated distribution of the topical composition as applied in FIG. 6.

FIG. 6 shows a series of computer-simulated images showing distribution of the cosmetic composition applied by iterating the method 300*b* of FIG. 3*b*. Each image in FIG. 6 is numerically numbered for the number of layers of the composition that is simulated to be applied. Similar to FIG. 5, each layer in FIG. 6 corresponds to one simulated pass of the device 100 across the entirety of the face of a user. As can be seen in FIG. 6, more of the cosmetic composition was simulated as being applied to regions of the face typically having darker areas of skin. FIG. 8 shows a computer-simulated image for an accumulated distribution of the cosmetic composition as applied in FIG. 6. As can be seen in FIG. 8, the cosmetic composition is simulated to be applied sparingly only to those areas that are darker than a selected tone—as shown by the forehead region not having any simulated accumulation of cosmetic composition, while the eye region, which typically has a darker appearance, shows an increased simulated accumulation of the cosmetic composition. FIG. 8 shows that the cosmetic composition is simulated to be directed towards those regions having skin artifacts that are within the middle spatial frequencies of the skin of the face of the user.

The invention described and claimed herein is not to be limited in scope by the specific embodiments herein disclosed since these embodiments are intended as illustrations of several aspects of this invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. All publications cited herein are incorporated by reference in their entirety.

What is claimed is:

1. A method for selectively applying a composition to skin of a user, comprising:

(a) obtaining, by a detector arrangement, image data corresponding to an image of an area of skin, the area of skin imaged by the detector arrangement;

(b) analyzing, by a processing arrangement, the image data to generate a reflectance value of the area of skin and a reflectance value of a location within the area of skin;

(c) comparing, by the processing arrangement, the reflectance value of the area of skin to: (i) a reflectance value of a selected tone, and (ii) the reflectance value of the location, wherein the reflectance value of the selected tone is generated based on image data corresponding to a region of skin adjacent to the area of skin; and (d) selectively applying, by an applicator arrangement, the composition to the location when the reflectance value of the area of skin is (i) less than the reflectance value of the selected tone, and (ii) greater than the reflectance value of the location.

2. The method of claim 1, wherein the reflectance value of the selected tone is generated based on past image data corresponding to the region of skin previously obtained by the detector arrangement.

3. The method of claim 1, wherein the reflectance value of the selected tone is generated based on past image data corresponding to images of a plurality of areas of skin previously imaged by the detector arrangement.

4. The method of claim 3, wherein the reflectance value of the selected tone is generated as a function of a reflectance value of a previously selected tone and the past image data.

5. The method of claim 3, further comprising:

(e) updating the past image data to include the image data corresponding to the area of skin imaged in step (a); and (f) repeating steps (a) through (d) for a further area of skin using the updated past image data.

6. The method of claim 3, wherein the past image data corresponds to an area imaged immediately prior to the area of skin imaged in step (a).

7. The method of claim 3, wherein the past image data corresponds to an area imaged adjacent to the area of skin imaged in step (a).

8. The method of claim 1, wherein step (c) comprises:

(1) determining, by the processing arrangement, whether $R_{area}-R_{location}>0$, and (2) determining, by the processing arrangement, whether $R_{area}-R_{location}>R_{area}-R_{tone}$, wherein $R_{area}$ is the reflectance value of the area of skin, $R_{location}$ is the reflectance value of the location, and $R_{tone}$ is the reflectance value of the selected tone, and wherein step (d) applies the composition, by the applicator arrangement, to the location when both (1) and (2) are met.

9. The method of claim 1, wherein the processing arrangement in step (c) further compares a difference of the reflectance value of the area of skin and the reflectance value of the location to a predetermined percentage of a difference of a reflectance value of the composition and the reflectance value of the location, and the applicator arrangement in step (d) applies the composition to the location when (i) the reflectance value of the area of is less than the reflectance value of the selected tone, (ii) the reflectance value of the area is greater than the reflectance value of the location, and (iii) the reflectance value of the area of skin and the reflectance value of the location is less than the predetermined percentage of a different of a reflectance value of the composition and the reflectance value of the location.

10. The method of claim 9, wherein the predetermined percentage is selected to identify skin artifacts within middle spatial frequencies of the skin of the user.

11. The method of claim 9, wherein step (c) comprises:

(1) determining, by the processing arrangement, whether $R_{area}-R_{location}>0$ and $R_{area}-R_{location}<z(R_{composition}-R_{location})$, and (2) determining, by the processing arrangement, whether $R_{area}-R_{location}>R_{area}-R_{tone}$, wherein $R_{area}$ is the reflectance value of the area of skin, $R_{location}$ is the reflectance value of the location, $R_{composition}$ is the reflectance value of the composition, $R_{tone}$ is the reflectance value of the selected tone, and z is a value between 0 and 1 selected to identify skin artifacts within middle spatial frequencies of the skin of the user.

12. The method of claim 11, wherein z is from about 0.01 to about 0.3.

13. The method of claim 1, wherein the applicator arrangement selectively applies a fixed amount of the composition.

14. The method of claim 1, wherein the composition is a cosmetic composition comprising a reflectance modifying agent.

15. The method of claim 14, wherein the composition comprises an active ingredient for treating a skin condition.

* * * * *